United States Patent [19]

Birum et al.

[11] Patent Number: 4,713,489

[45] Date of Patent: Dec. 15, 1987

[54] PREPARATION OF N-SUBSTITUTED ARYLSULFONAMIDES

[75] Inventors: Gail H. Birum, Kirkwood; Richard F. Jansen, St. Louis, both of Mo.

[73] Assignee: Akzo America Inc., New York, N.Y.

[21] Appl. No.: 820,876

[22] Filed: Jan. 16, 1986

Related U.S. Application Data

[63] Continuation of Ser. No. 662,923, Oct. 19, 1984.

[51] Int. Cl.$^4$ ............................................ C07C 143/79
[52] U.S. Cl. ...................................................... 564/90
[58] Field of Search ........................................... 564/90

[56] References Cited

U.S. PATENT DOCUMENTS

| | | | |
|---|---|---|---|
| 2,186,262 | 5/1935 | Mitchell | 106/40 |
| 2,658,916 | 11/1953 | Krems | 564/90 |
| 2,757,156 | 7/1956 | Dazzi | 260/30.8 |
| 3,246,007 | 4/1966 | Meyer et al. | 260/307 |
| 4,378,444 | 3/1983 | Barenberg et al. | 524/169 |

OTHER PUBLICATIONS

*The Merck Index*—10th Edition, Martha Windholtz, editor, Merck and Co. Inc., Rahway, N.J., 1983, p. ONR-82.

*Organic Chemistry of Sulfur* by C. M. Suter, John Wiley and Sons, Inc. (1944), pp. 573-578.

*Primary Examiner*—Anton H. Sutto
*Attorney, Agent, or Firm*—Francis W. Young; Louis A. Morris

[57] ABSTRACT

N-substituted arylsulfonamides which comprises the steps of (a) reacting an aryl hydrocarbon with chlorosulfonic acid to form a crude chlorosulfonation reaction product, (b) adding said crude reaction product to a mixture comprising an aliphatic amine, an alkali or alkaline earth metal hydroxide and water to form an amidation reaction mixture, (c) maintaining the temperature of the amidation reaction mixture at between about 50° C. and 100° C. and the pH at above about 7 with stirring for a period of time of up to about 2 hours, and optionally (d) separating the resulting N-substituted arylsulfonamide from the amidation reaction product.

18 Claims, No Drawings

PREPARATION OF N-SUBSTITUTED ARYLSULFONAMIDES

This is a continuation of application Ser. No. 662,923, filed Oct. 19, 1984.

BACKGROUND OF THE INVENTION

This invention relates to an improved process for the synthesis of N-substituted arylsulfonamides. More particularly, the invention relates to the preparation of N-substituted arylsulfonamides by reacting an aliphatic amine with the crude reaction product from the reaction of an aryl hydrocarbon and chlorosulfonic acid without separation of by-products or unreacted materials from the aryl sulfonyl chloride present in the crude reaction product.

A typical method for the preparation of N-alkyl substituted arylsulfonamides as set forth in *The Organic Chemistry of Sulfur* involves the use of an aryl sulfonyl chloride compound, generally prepared from the reaction of chlorosulfonic acid with a suitable aryl compound such as benzene, alkyl substituted benzene compounds, naphthalene and the like. The aryl sulfonyl chloride is reacted with a primary or secondary alkyl amine including cyclic amines such as piperidine and polymethylenediamines. The reaction is usually conducted in an inert solvent such as benzene, employing two equivalents of amine for one of the sulfonyl chloride, or in the presence of aqueous alkali where only one equivalent of amine may be necessary. Where the starting ingredients are a solid, the addition of an organic solvent immiscible with water is usually desirable. Alternatively, the reaction may also be carried out in the presence of triethyl amine or pyridine.

In order to avoid contamination, maintain sufficient yields and avoid the possibility of undesirable side reactions, the aryl sulfonyl chloride is typically refined, usually by water quenching, washing in the presence of a solvent, solvent stripping, distillation, and sometimes crystallization, to remove by-products and unreacted ingredients which may be present from the preparation of the aryl sulfonyl chloride.

U.S. Pat. No. 2,757,156 to Dazzi discloses preparation of N-alkyl alkene sulfonamides by reacting a paraffin with a mixture of sulfur dioxide and chlorine followed by reacting the resulting sulfonyl chloride with a primary alkyl amine. In an example, N-heptane sulfonyl chloride is prepared and then recovered by distillation of the reaction product prior to reaction with monoethylamine.

U.S. Pat. No. 3,246,007 to Meyer et al discloses oxadiazole benzene sulfonamide compounds. In the examples, the intermediate benzene sulfonyl chloride is isolated and purified prior to reaction with the amines.

Such refined aryl sulfonyl chloride is usually considered particularly important where the N-substituted aryl sulfonamide is to be used as a polymer-modifying additive, e.g., plasticizer or crystallizer in the preparation of molded compositions.

It has now been found that N-substituted aryl sulfonamides may be prepared without the multistep and costly purification of the aryl sulfonyl chloride intermediate and still function adequately in polymer modification of molded products.

SUMMARY OF THE INVENTION

The invention is a process for the preparation of N-substituted arylsulfonamides which comprises the steps of (a) reacting an aryl hydrocarbon with chlorosulfonic acid to form a crude chlorosulfonation reaction product containing an aryl sulfonyl chloride, (b) combining said crude chlorosulfonation reaction product, an aliphatic amine, an alkali or alkaline earth metal hydroxide and water in reactive contact to form an amidation reaction mixture, (c) maintaining the temperature of the reaction mixture at between about 50° C. and 100° C. and the pH at above about 7 for a period of time sufficient to form an amidation reaction product containing an arylsulfonamide and optionally (d) separating the resulting N-substituted arylsulfonamide from the amidation reaction product.

In a particular aspect of the invention, N-alkyl toluenesulfonamides are prepared by the steps of: (a) reacting toluene with chlorosulfonic acid to form a crude chlorosulfonation reaction product containing toluene sulfonyl chloride, (b) combining said crude reaction product, an alkyl amine, an alkali metal hydroxide and water in reactive contact to form an amidation reaction mixture, (c) maintaining the temperature of the reaction mixture at between about 50° C. and 100° C. and the pH at above about 7 for a period of time sufficient to form an amidation reaction product containing an N-alkyl toluenesulfonamide, and optionally (d) separating the resulting N-alkyl toluenesulfonamide from the amidation reaction product.

DESCRIPTION OF THE PREFERRED EMBODIMENTS

The process of the invention may be illustrated by the following reaction sequence wherein R is an alkyl group of from 1–20 carbon atoms and toluene is used as an example of the aromatic hydrocarbon.

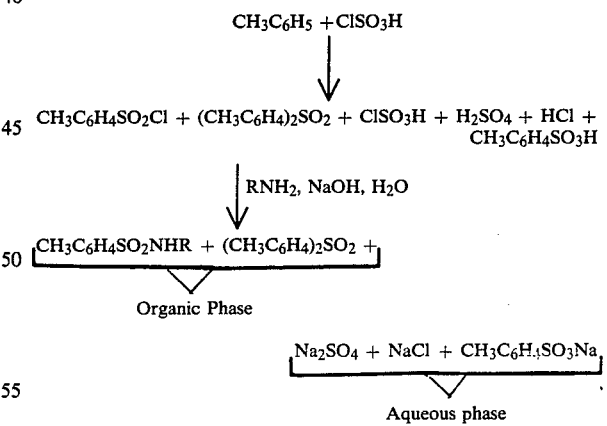

This process improvement avoids the multistep operation used to separate and refine the aryl sulfonyl chloride in the crude reaction product which is typically carried out. In the process of the present invention, in one step, the aryl sulfonamide is formed directly from the crude reaction product and the acidic by-products in said crude reaction product are neutralized. The process is of particular advantage where high molecular weight intermediates are involved since such intermediates are difficult to separate and purify by the usual distillation procedure.

The process of the invention begins with the reaction of an aryl hydrocarbon with chlorosulfonic acid to form a crude chlorosulfonation reaction product containing an arylsulfonyl chloride. Usually from about 2.4 to about 3.5 moles of chlorosulfonic acid are used per 1.0 mole of aryl hydrocarbon. The reaction takes place at ambient temperatures under nitrogen and total reaction time is from about 2 to 6 hours.

The aryl hydrocarbon may be any aryl hydrocarbon ring compound which is suitable for reaction with the chlorosulfonic acid, for example, benzene, toluene, cumene, orthoxylene, ethyl benzene, n-propyl benzene, n-butyl benzene, n-hexyl benzene, n-octyl benzene, n-nonyl benzene, or other alkyl substituted benzene compounds, naphthalene and substituted naphthalenes and the like. Benzene and toluene are preferred with toluene being especially preferred. The chlorosulfonic acid should be substantially pure since more than trace amounts of impurities may cause undesirable side reactions.

The crude chlorosulfonation reaction product formed by the reaction of chlorosulfonic acid and the aryl hydrocarbon comprises a mixture of, for example, in the case of toluene as the aryl hydrocarbon, a major portion of toluene sulfonyl chloride isomers (principally ortho and para), and minor amounts of bis-tolylsulfone, unreacted chlorosulfonic acid, sulfuric acid, hydrochloric acid and toluene sulfonic acid. The specific composition and percentages of ingredients in the crude reaction product will, of course, vary with the type of aryl hydrocarbon employed in the reaction and the ratio of reactants used.

The crude chlorosulfonation reaction product containing the arylsulfonyl chloride is next combined with an aliphatic primary or secondary amine, an alkali or alkaline earth metal hydroxide and water where the N-substituted sulfonamide is formed and the resulting acidic by-products neutralized.

The aliphatic primary amine may be any alkyl or alkenyl substituted amine wherein the substituent contains from 1 to 20 carbon atoms and mixtures thereof. Suitable alkyl amines include methylamine, ethylamine, n-propylamine, isopropylamine, n-butylamine, n-hexylamine, n-octylamine, n-decylamine, dodecylamine, butadecylamine, pentadecylamine, hexadecylamine, heptadecylamine, octadecylamine, eicosylamine and mixtures thereof. Alkyl amines containing from 14 to 18 carbon atoms are preferred. Especially preferred are tallow amines which are mixtures usually containing from about 60 to 70 wt. % octadecyl, preferably about 65 wt. %, from about 25 to 35 wt. % hexadecyl, preferably about 30 wt. %, from about 2 to 10 wt. % tetradecyl, preferably about 5 wt. %, and from trace amounts up to about 3 wt. % of other 12 to 20 carbon alkyl amines.

Alkenyl amines such as allylamine, 3-butenylamine, 2-butenylamine, 2-pentenylamine, 3-hexenylamine, 2-octenylamine, 4-decenylamine, 2-dodecenylamine, 8-tetradecenylamine, 9-hexadecenylamine, 9-octadecenylamine and mixtures thereof may also be used in the formation of the amide linkage.

The process is also applicable to secondary amines having alkyl substituents of 1 to 20 carbon atoms, e.g., dimethylamine, di-n-butylamine, didodecylamine and dioctadecylamine.

Neutralization of the acids formed during the chlorosulfonation step and during the amidation step may be effected by any suitable means compatible with the reaction. Alkali or alkaline earth metal hydroxides may be used. The alkali metal hydroxides include sodium hydroxide, potassium hydroxide and lithium hydroxide. Alkaline earth metal hydroxides such as magnesium hydroxide and calcium hydroxide may also be used. Sodium hydroxide is preferred.

The temperature of the amidation reaction mixture is maintained at between about 50° C. and 100° C., preferably, between about 60° C. and 90° C. by heating or cooling as needed or by rate of mixing. The heat of reaction will usually be sufficient to maintain the desired temperature with little or no additional heating being required. The pH of the amidation reaction mixture is maintained in a basic condition, i.e., above about 7 and, most preferably, between 9 and 11. In order to insure completion of the reaction, the temperature is maintained at reaction level after sulfonyl chloride addition is complete for a period of time of from about 30 minutes up to 2 hours or more, depending on the reactants involved.

In conducting the process of the invention, the proportions of reactants are based on the amount of aryl hydrocarbon used. Generally, from about 1.5 to about 4.0 moles, preferably 2 to 3 moles, of chlorosulfonic acid and from about 0.5 to about 0.9 moles, preferably 0.6 to 0.8 moles, of amine are used for each mole of aryl hydrocarbon. Sufficient hydroxide, usually about 5.0 to 7.0 moles, is used to neutralize all of the acid present and keep the pH at 7 or higher.

The overall process is preferably conducted as a batch procedure with the reaction of the chlorosulfonic acid with the aryl hydrocarbon taking place in one reaction vessel followed by addition of the crude chlorosulfonation reaction product to a second vessel containing the amine and other ingredients.

Isolation of the resulting N-alkyl or alkenyl substituted arylsulfonamide product is convenient due to the fact that the amidation reaction product readily separates into two layers; an aqueous layer usually containing mostly by-products and an organic layer rich in the desired product. The aqueous layer is easily removed by siphoning. The organic layer containing the N-arylsulfonamide may be separated and used without further purification or it may be washed one or more times with water or with water made basic with sodium hydroxide, sodium carbonate, potassium hydroxide or potassium carbonate. Usually about three such washes are the maximum needed to remove the acidic and salt by-products. The product may then be dehydrated by heating (from room temperature) up to 150° C., preferably 100° C. to 130° C., at reduced pressure, for example 0.1 to 100 mm Hg (13.33 to 13.332 Pa), preferably 20 to 50 mm Hg (2666 to 6666 Pa). Filtration of the product while it is in the molten state is sometimes used to remove traces of suspended salts.

The products of the process of this invention are usually mixtures of isomers, largely ortho-and para-substituted, and lesser amounts of meta isomers and of sulfones. In general, from about 40 to 80 percent para, from about 20 to 55 percent ortho and from 1 to about 4 percent meta isomers, all by weight, will be present in such mixtures. Small amounts of inert sulfone by-products, from about 1 to about 3 weight percent, may exist in the product. The process is particularly useful when such product mixtures can be used without further purification, e.g., in plasticizer applications.

The invention is further illustrated by the following examples in which all parts and percents are by weight unless otherwise indicated.

EXAMPLE 1

Preparation of N-tallow Toluenesulfonamide

A 1 liter flask equipped with a stirrer, thermometer, dropper addition funnel and water cooled reflux condenser with the outlet connected to a water scrubber, was charged with 2.5 moles (291.3 gms) of chlorosulfonic acid. The addition funnel was charged with 1.0 mole (92.1 gms) of toluene. With rapid stirring and some cooling with a dry ice isopropyl alcohol bath, the toluene was added to the chlorosulfonic acid during a 1 hour period at 20° C. to 25° C. The system was kept under $N_2$ at all times. Ten minutes after the addition was completed, a test sample was removed for proton NMR analysis. The mixture was stirred for two hours at 20° C. to 25° C., then another small test sample was removed for proton NMR analysis. Sample 1 showed the reaction essentially completed, Sample 2 showed the formation of some by-product.

Next, a 3 liter flask equipped as above was charged with 0.9 moles (240.4 gms) of hydrogenated tallow amine, a primary amine containing a mixture of alkyl groups (65 percent of the mixture being octadecyl, 30 percent hexadecyl and 5 percent tetradecyl), 4.0 moles of sodium hydroxide (320 gms of a 50% solution) and 1.5 liters of tap water. The crude toluene sulfonyl chloride mixture from above was charged to the addition funnel. The mixture in the flask was stirred and warmed to 80° C., and the crude sulfonyl chloride was added from the funnel over a period of 1½ hours with the temperature maintained at 80° C. to 90° C. by heat of reaction. When the addition was completed, enough additional sodium hydroxide (50.6 gms) was added to raise the pH to 10. The mixture was warmed and stirred at 80° C. to 85° C. at the pH of 10 for 45 minutes, and then the stirrer was stopped to allow layers to separate. The aqueous phase, the lower layer, was siphoned off and discarded. The organic, oily product layer was washed four times with 600 ml of tap water at 85° C., and then dehydrated by stirring and warming under vacuum (water aspirator) at a pot temperature of 125° C. for ½ hour. The product was filtered while hot and then poured onto a teflon-coated pan and allowed to cool, giving 338 gms (89% yield) of a yellow waxy solid.

Proton NMR analysis in $CDCl_3$ is consistent with the N-tallow toluenesulfonamide structure.

EXAMPLE 2

Preparation of N-butyl octylbenzenesulfonamide

A 1 liter flask equipped with a stirrer, thermometer, dropper addition funnel and dry ice cooled reflux condenser was charged with 1.32 moles (153.0 gms) of chlorosulfonic acid. The addition funnel was charged with 100 gms (0.53 moles) of 1-phenyloctane which was added to the stirred chlorosulfonic acid under a nitrogen blanket over a 40 minute period at 20° C. to 30° C. Some cooling with a cold water bath was required and the mixture was stirred at 25° C. for 4 hours. The resulting product was then added to a stirred mixture of 0.53 moles (38.4 gms) of n-butyl amine, 216 gms of 50 percent sodium hydroxide (2.7 moles) and 300 mls of tap water in one hour at 60° C. to 65° C. The pH of the mixture was checked periodically to be sure that it remained above 10. After the addition was completed, the mixture was stirred at 60° C. to 65° C. with the pH maintained above 10 for 1.25 hours. The aqueous phase was allowed to settle and then siphoned off and discarded. The oily organic layer was washed with 2% hydrochloric acid, 5% sodium carbonate solution, and four times with deionized water, and then dehydrated at 120° C. at 25 mm Hg (3333 Pa) and filtered, giving 88 gms (52% yield) of clear, brown liquid product having a proton NMR spectra consistent with the N-butyl octylbenzenesulfonamide structure.

EXAMPLE 3

Preparation of N-ethyl Cyclohexylbenzene Sulfonamide

A 1 liter flask equipped as in Example 2 was charged with 254 gms (2.18 moles) of chlorosulfonic acid, and then 100 gms (0.62 moles) of phenylcyclohexane was added to the stirred chlorosulfonic acid over a 1½ hour period at 25° C. to 30° C. under $N_2$. The mixture was stirred at 25° C. under $N_2$ for 4 hours and then it was added to a mixture of 376 gms of 50 percent sodium hydroxide (4.7 moles), 500 mls of deionized water and 40 gms (0.62 moles) of 70 percent ethylamine at 40° C. to 50° C. over a 2 hour period at a pH above 10. The cooled reaction mixture was filtered to isolate a tan solid which was then washed with water and recrystallized from cyclohexane to give 48.7 gms (28.9% yield), m.p. 100°–101.5° C., proton NMR consistent with N-ethyl cyclohexylbenzene sulfonamide structure.

EXAMPLE 4

Preparation of N-ethyl Toluenesulfonamide

A 1 liter flask equipped as for Example 3 was charged with 3.5 moles (407.8 gms) of chlorosulfonic acid, and 1.0 mole (92.1 gms) of toluene was added over a ½ hour period under $N_2$ at 25° C. to 30° C. Stirring and cooling with an external cold water bath was required. The reaction mixture was then stirred at 25° C. under $N_2$ for 4 hours. The resulting crude sulfonyl chloride mixture was added to a solution of 1.0 mole of ethylamine and 294 gms of NaOH in 900 ml of deionized water at 45° C. to 55° C. over a 2 hour period. The mixture was stirred at 55° C. and at a pH above 10 for 1 hour after the addition was completed.

After standing overnight, the organic phase was separated, washed with water, decolorized with potassium permanganate and sodium meta bisulfite, washed with sodium carbonate solution and water, and dehydrated at 125° C. and 0.2 mm Hg (26.66 Pa), giving 123g (61.7% yield) of light yellow liquid. Proton NMR in $CDCl_3$ was consistent with the N-ethyl toluene sulfonamide structure. GC analysis showed 43.5 percent ortho and 53.3 percent para-N-ethyl toluene sulfonamide plus 2.4 percent tolyl sulfones.

EXAMPLE 5

Preparation of N-ethyl Isopropylbenzene Sulfonamide

A 1 liter flask equipped with a stirrer, thermometer, dropper addition funnel and a water cooled reflux condenser was charged with 3.5 moles of chlorosulfonic acid (407.8 gms), and 1.0 mole (120.2 gms) of cumene (isopropylbenzene) was added under $N_2$ to the stirred chlorosulfonic acid at 25° C. to 30° C. with cooling via external water bath over a ½ hour period. The mixture was then stirred at room temperature (23° C.) for 6 hours. The crude product was added to a solution of 500 mls of tap water, 128.8 gms of 70 percent ethylamine (2.0 moles of amine) and 50 mls of 50 percent sodium hydroxide with monitoring of pH and maintaining the temperature at 55° C. to 60° C. with an external ice water bath. When the pH reached 8.0, simultaneous addition of 50 percent sodium hydroxide was begun and the pH was controlled at 7.9 to 8.4 by the rate of addition throughout the rest of the reaction. The total addition was completed in about 1 hour. The amount of 50 percent sodium hydroxide consumed including the initial charge was 521.2 gms (260.0 g of NaOH-6.5 moles). The mixture was stirred at 60° C. for ½ hour with the pH remaining at 8 and then decolorized by permanganate and sodium meta bisulfite treatment, acid and base washed, and dehydrated by stirring and warming under vacuum to a final pot temperature of 120° C. and a pressure of 0.5 mm of mercury (66 Pa) to give 169.3 gms (74.5 percent yield based on the amount of starting cumene) of light yellow solid. Proton NMR in CDCl$_3$ was consistent with the N-ethyl isopropylbenzene sulfonamide structure. The GC analysis indicated 96.4 percent sulfonamide which was 16.4 percent ortho, 6.3 percent meta and 77.3 percent para. The analysis also showed 2.0 percent sulfones.

EXAMPLE 6

Preparation of N-ethyl Nonylbenzene Sulfonamide

A 1 liter flask equipped as in Example 5 was charged with 1.72 moles (200.4 gms) of chlorosulfonic acid, and 0.49 moles (100 gms) of 1-phenylnonane was added to the vigorously stirred chlorosulfonic acid under N$_2$ in 2 hours at 20° C. to 25° C. with cold water bath cooling. The mixture was stirred at 25° C. for ½ hour, then left to stand at room temperature under N$_2$ overnight. The resulting crude sulfonyl chloride mixture was then added to a solution of 0.98 mole of ethylamine and 3.22 mole of NaOH in 275 ml of water in 0.5 hours at 55° C.±2°. The temperature was maintained at 55-°60° for 0.5 hour more with the pH above 10. Working up of the reaction mixture as in Example 5 gave 74.8 gms (49% yield) of amber liquid having a proton NMR spectra in CDCl$_3$ consistent with the desired structure. The acidity of the product was 1.68 meq. per 100 gms. GC analysis showed that it was 98.8 percent sulfonamide (27.1 percent ortho, 5.7 percent meta and 67.2 percent para isomers).

EXAMPLE 7

Preparation of N-tallow Toluenesulfonamide from Purified Toluenesulfonyl Chloride Chlorosulfonic acid and toluene (2.4 to 1 molar ratio) are fed in separate streams onto the surface of an agitated heel of crude toluenesulfonyl chloride mixture from a previously prepared chlorosulfonation batch held at 25°-30° C. in a 2000 gal. reactor. The crude chlorosulfonation mixture is then fed into a quenching vessel along with chilled water and toluene. The quenched product overflows into a quencher separator where the aqueous acid comes to the top and overflows into an acid neutralizing vessel. The quenched organic layer is pumped to a two stage washing system to remove acid contamination and then into a jacketed glass-lined dehydrator where dehydration is carried out under 25 mm Hg vacuum and 80° C. pot temperature. The dehydrated product then goes into a detoluenation still where the remaining toluene is removed under 17-19 mm Hg and pot temperature of 124°-126° C. The detoluenated product is then fed into a still where a purified mixture of toluenesulfonyl chloride isomers (about 65% para, 34% ortho, and 1% meta) is separated, leaving sulfones and other undesired residues for disposal.

A 230.2 gms (1.21 moles) portion of the purified toluenesulfonyl chloride isomer mixture is warmed to the molten state and then added dropwise to a stirred mixture of 315.0 gms (1.18 moles) of hydrogenated tallow amine, 24.0 g (0.6 mole) of NaOH, and 525 ml of water at 80°-85° C. When the pH decreased to 7.8, additional 50% NaOH was added simultaneously to maintain the pH at 8.0-8.5. The total sulfonyl chloride addition time was 2 hours. The reaction mixture was stirred at 80°-85° C. for 1.5 hours more as the pH was kept at 8-11. The aqueous salt layer was removed, and the organic product layer was washed three times at 80°-85° C. with 500 ml of water and then dehydrated by warming to 120°/0.7 mm Hg (93 Pa), leaving 478.6 gms (95.5% yield) of yellow oil which solidified to a waxy solid.

EXAMPLE 8

Preparation of N-tallow Toluenesulfonamide from Crude Unrefined Chlorosulfonation Mixture In a demonstration of the advantages of using the crude, unrefined chlorosulfonation intermediate of the present invention instead of the purified toluenesulfonyl chlorides obtained by the complex, multistep quenching, washing, dehydration, detoluenation and distillation process described in Example 7, a 794.4 gms portion of the crude chlorosulfonation intermediate of Example 7 was added to a stirred mixture of 300.4 gms of hydrogenated tallow amine, 1200 ml of water and 869 gms of 50% NaOH in 2.25 hours at 80°-90° C. Warming was continued at 85°-90° C. for 1.5 hours while maintaining the pH at 10-11, and the organic product layer was washed three times at 80°-85° C. with 600 ml of water and then dehydrated by warming to 125° C./1.0 mm Hg (133 Pa), leaving 473.7 gms (100% yield) of amber oil which solidified to a waxy solid. Analysis of this product showed that it contained 1.8% sulfones, this being the only significant difference from the product obtained by the multistep process of Example 7.

Comparison of products obtained by the process of Example 7 and of this example as modifying additives in polyethylene terephthalate polymer showed that they were equivalent within experimental error.

Although this invention has been described with respect to specific embodiments, the details thereof are not to be construed as limitations, for it will be apparent that various equivalents changes and modifications may be resorted to without departing from the spirit and scope thereof and it is understood that such equivalent embodiments are intended to be included herein.

We claim:

1. A process for the preparation of N-substituted arylsulfonamides comprising the steps of: (a) reacting an aryl hydrocarbon with chlorosulfonic acid to form a crude chlorosulfonation reaction product, (b) combining said crude reaction product, an aliphatic amine, an alkali metal hydroxide or alkaline earth metal hydroxide and water in reactive contact to form an amidation reaction mixture, (c) maintaining the temperature of the amidation reaction at between about 50° C. and 100° C. and the pH at above about 7, for a period of time sufficient to form an amidation reaction product comprising an organic phase and an aqueous phase, said organic phase being rich in N-substituted arylsulfonamide, and said aqueous phase containing mostly by-products of said amidation reaction product, (d) separating said organic phase from said aqueous phase and (e) recovering said N-substituted arylsulfonamide from said organic phase.

2. The process of claim 1 wherein the aryl hydrocarbon is an alkyl benzene compound wherein the alkyl group contains from 1 to 15 carbon atoms.

3. The process of claim 2 wherein the alkyl group is selected from methyl, ethyl, n-butyl, isopropyl, octyl and cyclohexyl.

4. The process of claim 1 wherein the aliphatic amine is an alkkyl amine selected from ethyl amine, n-butyl amine and tallow amine.

5. The process of claim 1 wherein the alkali metal hydroxide is sodium hydroxide.

6. The process of claim 1 wherein the temperature is 60 °C. to 90° C.

7. The process of claim 1 wherein the pH is from about 9 to about 11.

8. The process of claim 1 wherein from about 1.5 to 4.0 moles of chlorosulfonic acid, about 0.5 to 0.9 moles of aliphatic amine and about 5.0 to 7.0 moles of alkali metal hydroxide or alkaline earth metal hydroxide are used for each mole or aryl hydrocarbon.

9. A process for the preparation of N-alkyl toluene sulfonamides comprising the steps of: (a) reacting toluene with chlorosulfonic acid to form a crude chlorosulfonation reaction product containing toluene sulfonyl chloride, (b) combining said crude reaction product, an alkyl amine, an alkali metal hydroxide and water in reactive contact to form an amidation reaction mixture, (c) maintaining the temperature of the amidation reaction mixture at between about 50° C. and 100° C. and the pH at above 7 for a period of time of from 30 minutes up to about 2 hours to form an amidation reaction product comprising an organic phase and an aqueous phase, said organic phase being rich in N-alkyl toluene sulfonamide and said aqueous phase containing mostly by-products of said amidation reaction product, (d) separating said organic phase from said aqueous phase and (e) recovering said N-alkyl toluene sulfonamide from said organic phase.

10. The process of claim 9 wherein the alkyl amine is tallow amine.

11. The process of claim 9 wherein the alkyl amine is hydrogenated tallow amine.

12. The process of claim 9 wherein the alkali hydroxide is sodium hydroxide.

13. The process of claim 9 wherein the temperature is from about 60° C. to 90° C.

14. The process of claim 9 wherein the pH is from about 9 to 11.

15. The process of claim 9 wherein the separation comprises at least 1 aqueous washing step.

16. The process of claim 9 wherein the N-alkyl toluene sulfonamide product comprises from about 40 to 80 percent para isomers, from about 20 to 55 percent ortho isomers and from about 1 to 4 percent meta isomers.

17. The process of claim 9 wherein the N-alkyl toluene sulfonamide product contains from about 1 to about 3 weight percent tolylsulfones.

18. The process of claim 9 further including purifying said sulfonamide product by means of at least one water washing followed by dehydration at up to 150° C. and at a reduced pressure of from about 0.1 mm (13 Pa) to 100 mm Hg (13332 Pa).

* * * * *